(12) United States Patent
Fröhling

(10) Patent No.: US 8,268,014 B2
(45) Date of Patent: *Sep. 18, 2012

(54) HAIR DYEING COMPOSITION

(75) Inventor: Beate Fröhling, Neustadt (DE)

(73) Assignee: BASF SE Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/148,685

(22) PCT Filed: Feb. 19, 2010

(86) PCT No.: PCT/EP2010/052097
§ 371 (c)(1),
(2), (4) Date: Sep. 30, 2011

(87) PCT Pub. No.: WO2010/097338
PCT Pub. Date: Sep. 2, 2010

(65) Prior Publication Data
US 2012/0017931 A1    Jan. 26, 2012

(30) Foreign Application Priority Data
Feb. 25, 2009 (EP) ................... 09153589

(51) Int. Cl.
*A61Q 5/10* (2006.01)
*C07D 265/00* (2006.01)
(52) U.S. Cl. ............ 8/405; 8/407; 8/409; 8/426; 8/466; 8/565; 8/567; 8/568; 8/570; 8/572; 8/574; 544/103
(58) Field of Classification Search ............. 8/405, 407, 8/409, 426, 466, 565, 567, 568, 570, 572, 8/574; 544/103
See application file for complete search history.

(56) References Cited

U.S. PATENT DOCUMENTS
3,369,970 A   2/1968 McLaughlin
6,190,421 B1   2/2001 Rondeau FOREIGN PATENT DOCUMENTS
DE   3829870 A1   4/1989
(Continued)

OTHER PUBLICATIONS
STIC Search Report dated Jan. 31, 2012.*
(Continued)

*Primary Examiner* — Eisa Elhilo
(74) *Attorney, Agent, or Firm* — Shiela A. Loggins

(57) ABSTRACT

The invention relates to hair dyeing composition comprising (a) a dye of formula (1); (b) ant least one dye selected from the compounds of formulae (2); (3) and (4); wherein D is the radical of a diazo component of the formula (2a); (2b); (2c); (2d); (2f); (2g) or (2h). The invention also relates to the dyeing methods for dyeing keratinous fibers comprising such dyeing composition.

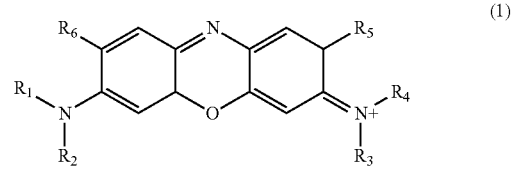

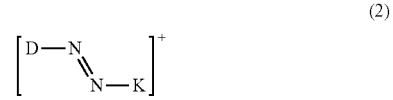

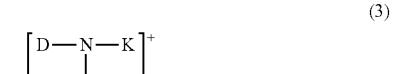

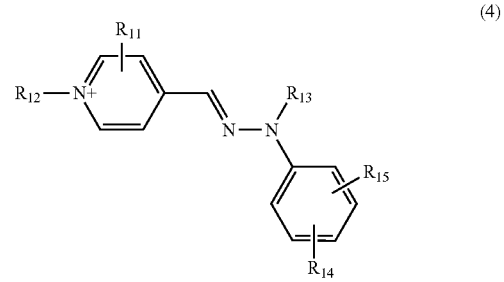

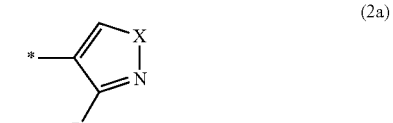

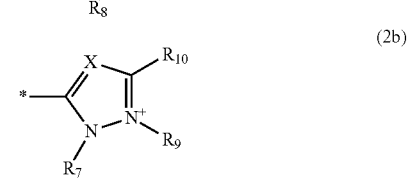

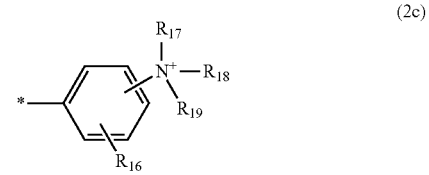

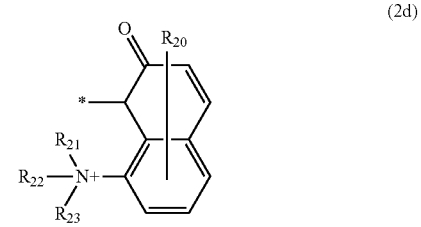

14 Claims, No Drawings

FOREIGN PATENT DOCUMENTS

| | | |
|---|---|---|
| DE | 19959479 A1 | 7/2001 |
| EP | 318 294 A2 | 5/1989 |
| EP | 714 954 A2 | 6/1996 |
| GB | 1 249 438 A | 10/1971 |
| GB | 1 408 734 A | 10/1975 |
| WO | 95/01772 A1 | 1/1995 |
| WO | WO 95/01772 * | 1/1995 |
| WO | 95/15144 A1 | 6/1995 |
| WO | 97/20545 A1 | 6/1997 |
| WO | 00/10519 A1 | 3/2000 |
| WO | 03/022233 A | 3/2003 |
| WO | 2004/019897 A1 | 3/2004 |
| WO | 2006/108458 A | 10/2006 |

OTHER PUBLICATIONS

J. F. Corbett: The Chemistry of Hair-Care Products, JSCD Aug. 1976, p. 290.
English Language Abstract of DE 19959479.
English Language Abstract of DE 3829870.
English Language Abstract of WO 00/10519.
English Language Abstract of EP 714 954.

* cited by examiner

HAIR DYEING COMPOSITION

The present invention relates to a composition for dyeing keratinous fibres, in particular human keratinous fibres such as hair, comprising, in an appropriate dyeing medium, at least a mixture of at least 2 cationic direct dyes of a given formula, compositions thereof, to processes for their preparation and to their use in the dyeing of organic material, such as keratin fibers, wool, leather, silk, cellulose or polyamides, especially keratin-containing fibres, cotton or nylon, and preferably hair, more preferably human hair.

It is known, for example, from WO 95/01772, WO 95/15144, EP 714 954 and EP 318 294 that cationic dyes can be used to dye organic material, for example keratin, silk, cellulose or cellulose derivatives, and also synthetic fibres, for example polyamides. Cationic dyes exhibit very brilliant shades. A disadvantage is their unsatisfactory fastness to hydrolysis and to light, their frequently inadequate stability under reducing or oxidizing conditions, and their frequently unsatisfactory storage stability (see: John F. Corbett: "The Chemistry of Hair-Care Products", JSCD August 1976, page 290).

The actual technical problem of the present invention was to provide brilliant dyes that are distinguished by deep dyeing having good fastness properties with respect to washing, light, shampooing and rubbing, and that preferably exhibit satisfactory stability under reducing or oxidizing dyeing conditions, for the dyeing of organic material.

Accordingly, the present invention relates to a hair dye composition, comprising
(a) a dye of formula

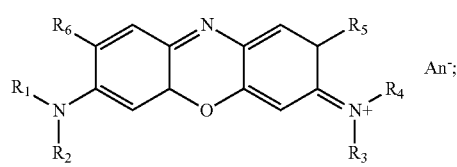
(1)

(b) at least one dye selected from the compounds of formulae

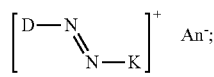
(2)

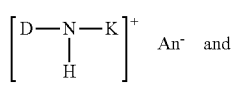
(3)

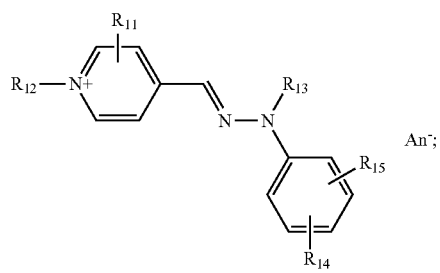
(4)

wherein
D is the radical of a diazo component of the formula

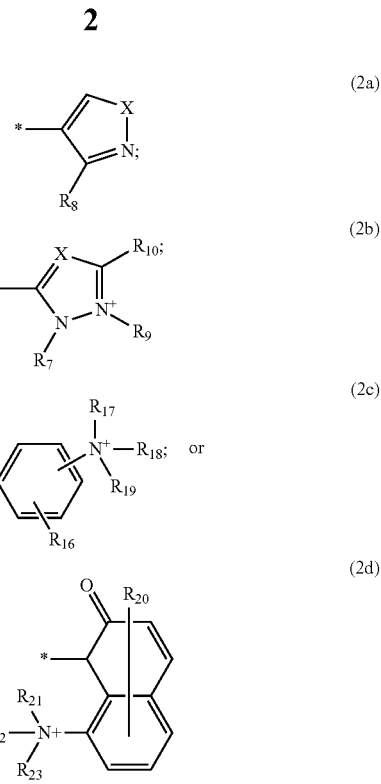

K is the radical of a coupling component selected from aniline derivatives; phenol derivatives; naphthalene derivative;
X is —CH= —O—; —S—; or —N($R_7$)—;
$R_1$, $R_2$, $R_3$ and $R_4$ independently from each other are hydrogen; or $C_1$-$C_4$alkyl;
$R_5$ and $R_6$ independently from each other are hydrogen; $C_1$-$C_4$alkyl; or $C_1$-$C_4$alkoxy;
$R_7$ and $R_9$ independently from each other are unsubstituted or OH—, $C_1$-$C_4$alkoxy-, halogen-, amino-, $C_1$-$C_4$-mono or -dialkylamino-substituted $C_1$-$C_4$alkyl; or phenyl;
$R_8$ is hydrogen; $C_1$-$C_4$alkyl; Cl; or nitro;
$R_{10}$ is hydrogen; $C_1$-$C_4$alkyl; Cl; nitro; amino; or $C_1$-$C_4$mono- or $C_1$-$C_4$dialkylamino;
$R_{11}$ is hydrogen; $C_1$-$C_4$alkyl; or CN;
$R_{12}$ is unsubstituted or OH— or CN-substituted $C_1$-$C_4$alkyl;
$R_{13}$ is hydrogen; or $C_1$-$C_4$alkyl;
$R_{14}$ and $R_{15}$ independently from each other are hydrogen; $C_1$-$C_4$alkyl; or $C_1$-$C_4$alkoxy; or
$R_{14}$ and $R_{15}$ together with the nitrogen and carbon atoms joining them together form a 5-or 6-membered ring;
$R_{16}$ and $R_{20}$ independently from each other are hydrogen; $C_1$-$C_4$alkyl; hydroxy; Cl; nitro; amino, $C_1$-$C_4$mono- or dialkylamino;
$R_{17}$, $R_{18}$, $R_{19}$, $R_{21}$, $R_{22}$ and $R_{23}$ independently from each other are hydrogen; or $C_1$-$C_4$alkyl;
$R_{24}$ is hydrogen; or $C_1$-$C_4$alkyl; and
An$^-$ is a colorless anion.

$C_1$-$C_{30}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl, tredecyl, tetradecyl, pentadecyl, haxadecyl or eicosyl.

$C_2$-$C_{30}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

Aryl is for example naphthyl and preferably phenyl.

Heterocyclic organic radical is, for example, a five-membered nitrogen-containing hetero-cyclic radical such as imidazolyl, pyrazolyl, triazolyl, pyrrolyl, pyrrolidinyl, oxazolyl or thiazolyl, a six-membered nitrogen-containing heterocyclic radical such as piperazinyl, piperidinyl, pyridinyl or morpholinyl, or a bicyclic radical which possesses a fused-on five-membered nitrogen-containing heterocycle and a six-membered aromatic ring, such as benzoxazolyl, indolyl, benzothiazolyl, benzimidazolyl or benzotriazolyl.

Preferred is a hair dye composition, wherein in formula (1) of component (a) $R_1$, $R_2$, $R_3$ and $R_4$ independently from each other are hydrogen; or $C_1$-$C_2$alkyl.

More preferred is a hair dye composition, wherein component (a) corresponds to formula <chemical structure> (5)

Preferably $R_8$ is hydrogen; or $C_1$-$C_4$alkyl.

More preferably, in formulas (2a) and (2b)

$R_7$ and $R_9$ independently from each other are $C_1$-$C_4$alkyl; and even more preferred are hair dye compositions, wherein in formula (2a)

X is —$NR_7$; and $R_8$ is hydrogen; or $C_1$-$C_4$alkyl.

Preferred are hair dye compositions, wherein

D is a radical of formula

<chemical structure> (2e)

<chemical structure> (2f)

<chemical structure> (2g)

<chemical structure> (2h)

Even more preferred are hair dye compositions, wherein in formulas (2)

K is the radical of formula

<chemical structure> (2i)

wherein $R_{25}$ is hydrogen; hydroxy; $C_1$-$C_4$alkyl; $C_1$-$C_4$alkoxy; nitro; amino; mono-$C_1$-$C_4$alkylamino; di-$C_1$-$C_4$alkylamino; or a radical of formula <chemical structure> wherein $R_{26}$, $R_{27}$ and $R_{28}$ independently from each other are hydrogen; or $C_1$-$C_4$alkyl.

Preferred are also hair dye compositions wherein

K is the radical of formula

<chemical structure> (2k)

Most preferred are hair dye compositions comprising
(a) a dye of formula (1), and
(b) at least one dye selected from the compounds of formulae <chemical structure> (6)

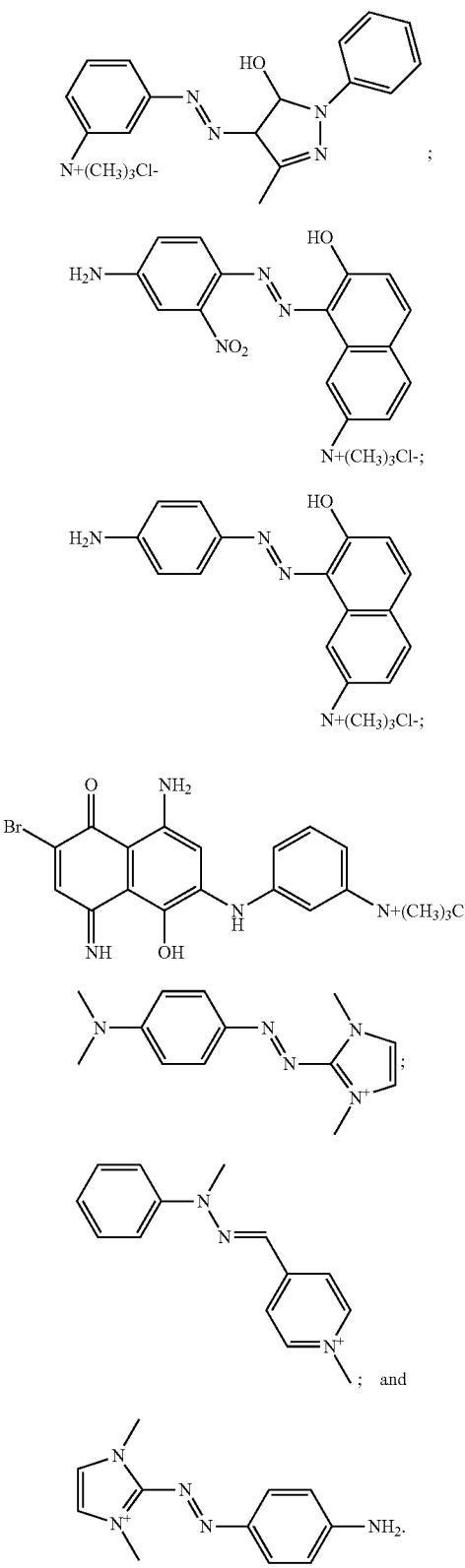
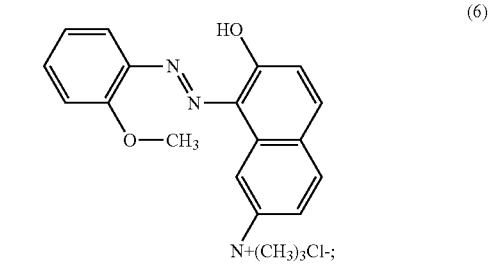
Preferred are also hair dying compositions, comprising
(a) a dye of formula (1), and
(b) at least one dye selected from the compounds of formulae
Also preferred are hair dying compositions, comprising
(a) a dye of formula (1), and
($b_1$) the dyes of formulae
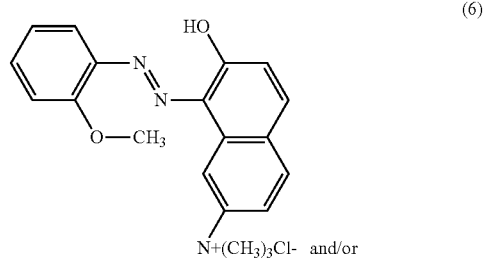

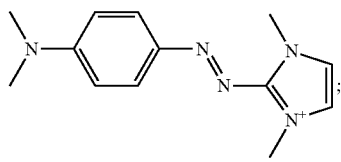

(11)

and
(b$_2$) the dye of formula

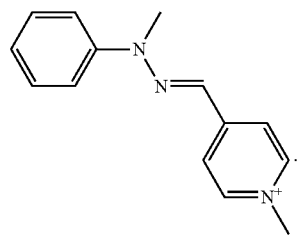

(12)

The hair dye compositions according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The stability, in particular the storage stability of the hair dye compositions according to the invention are excellent.

The multiplicity of shades of the dyes can be increased by combination with other dyes.

Therefore the hair dye compositions of the present invention may be combined with dyes of the same or other classes of dyes, especially with direct dyes, oxidative dyes; disulfide dyes, pigments or mixtures thereof.

Direct dyes are of natural origin or may be prepared synthetically. They are uncharged, cationic or anionic, such as acid dyes.

The hair dye composition according to the present invention of may be used in combination with at least one single direct dye different from the dyes of component (a) and (b).

Examples of direct dyes are described in "Dermatology", edited by Ch. Culnen, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie- und Handelsunternehmen für Arzneimittel, Reformwaren und Korperpflegemittel e.V., Mannheim.

Furthermore, cationic nitroaniline and anthraquinone dyes are useful for a combination with the hair dyeing composition according to the present invention.

The hair dye composition according to the present invention may also be combined with acid dyes, for example the dyes which are known from the international names (Color index), or trade names.

These acid dyes may be used either as single component or in any combination thereof.

The hair dye composition according to the present invention may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the hair dye composition according to the present invention may also be used in combination with sulfide dyes. Examples for sulfide dyes are disclosed for example in WO 05/097051.

Furthermore, the hair dye composition according to the present invention may also be used in combination with color pigments.

The organic pigments are preferably selected from D&C Red 30 (Vat Red 1); D&C Red 36 (Pigment Red 4); Carmine; D&C Red 6 Ba Lake; D&C Red 7 Ca Lake; D&C Red 30 Al Lake; D&C Red 30 Talc Lake; D&C Red 27 Al Lake; D&C Red 28 Al Lake; D&C Red 33 Al Lake; D&C Red 21 Al Lake.

Of specific interest are the pigments/colours listed in Table 1 below:

Table 1a: Examples of pigments/colours (component (b))

| Color index number | Official and common name | CAS registry number |
|---|---|---|
| 10006 | Pigment Green 8 | 16143-80-9 |
| 10020 | Acid Green 1 | 19381-50-1 |
| 10316 (2) | Ext. D & C Yellow No. 7; Acid Yellow 1; Naphthol Yellow S | 846-70-8 |
| 11680 | Pigment Yellow 1 | 2512-29-0 |
| 11710 | Pigment Yellow 3 | 6486-23-3 |
| 11725 | Pigment Orange 1 | 6371-96-6 |
| 11920 | Solvent Orange 1 | 2051-85-6 |
| 12010 | Solvent Red 3 | 6535-42-8 |
| 12085 (2) | D & C Red No. 36; Pigment Red 4; Flaming Red | 2814-77-9 |
| 12120 | Pigment Red 3 | 2425-85-6 |
| 12150 | Solvent Red 1 | 1229-55-6 |
| 12370 | Pigment Red 112 | 6535-46-2 |
| 12420 | Pigment Red 7 | 6471-51-8 |
| 12480 | Pigment Brown | 6410-40-8 |
| 12490 | Pigment Red 5 | 6410-41-9 |
| 12700 | Disperse Yellow 16 | 4314-14-1 |
| 13015 | E 105; Acid Yellow 9 | 2706-28-7 |
| 14270 | E 103; Acid Orange 6 | 547-57-9 |
| 14700 | FD & C Red No. 4; Food Red 1; Ponceau SX | 4548-53-2 |
| 14720 | E 122; Acid Red 14; Food Red 3; Azorubine; Carmoisine | 3567-69-9 |
| 14815 | E 125; Food Red 2 | 3257-28-1 |
| 15510 (2) | D&C Orange No. 4; Acid Orange 7; Orange II | 633-96-5 |

-continued

| | | |
|---|---|---|
| 15525 | Pigment Red 68 | 5850-80-6 |
| 15580 | Pigment Red 51 | 227-459-1 |
| 15620 | Acid Red 88 | 1658-56-6 |
| 15630 | Pigment Red 49 | 1248-18-6 |
| 15800:1 | D&C Red No. 31; Pigment Red 64:1; Brilliant Lake Red R | 6371-76-2 |
| 15850 | D&C Red No. 6; Pigment Red 57; Lithol Rubin B | 5858-81-1 |
| 15850:1 (2) | D&C Red No. 7; Pigment Red 57:1; Lithol Rubin B Ca | 5281-04-9 |
| 15865 (2) | Pigment Red 48 | 3564-21-4 |
| 15880:1 | D&C Red No. 34; Pigment Red 63:1; Deep Maroon; Fanchon Maroon; Lake Bordeaux B | 6417-83-0 |
| 15980 | E 111; Food Orange 2 | 2347-72-0 |
| 15985 (2) | FD&C Yellow No. 6; E 110; Food Yellow 3; Sunset Yellow; Sunset Yellow FCF; Orange Yellow S | 2783-94-0 |
| 16035 | FD&C Red No. 40; Food Red 17; Allura Red; Allura Red AC | 25956-17-6 |
| 16230 | Acid Orange 10 | 1936-15-8 |
| 16255 (2) | E 124; Acid Red 18; Food Red 7; Ponceau 4R; Cochineal Red A | 2611-82-7 |
| 16290 | E 126; Acid Red 41 | 5850-44-2 |
| 17200 (2) | D&C Red No. 33; Acid Red 33; Acid Fuchsine | 3567-66-6 |
| 18050 | Acid Red 1 | 3734-67-6 |
| 18130 | Acid Red 155 | 10236-37-0 |
| 18690 | Acid Yellow 121 | 5601-29-6 |
| 18736 | Acid Red 180 | 6408-26-0 |
| 18820 | Acid Yellow 11 | 6359-82-6 |
| 18965 | Acid Yellow 17 | 6359-98-4 |
| 19140 (2) | FD&C Yellow No. 5; E 102; Acid Yellow 23; Tartrazine | 1934-21-0 |
| 20040 | Pigment Yellow 16 | 5979-28-2 |
| 20170 | D&C Brown No. 1; Acid Orange 24; Resorcin Brown | 1320-07-6 |
| 20470 | Noir W 699 | 1064-48-8 |
| 21100 | Pigment Yellow 13 | 5102-83-0 |
| 21108 | Pigment Yellow 83 | 5567-15-7 |
| 21230 | Solvent Yellow 29 | 6706-82-7 |
| 24790 | Acid Red 163 | 13421-53-9 |
| 26100 | D&C Red No. 17; Solvent Red 23; Sudan III; Toney Red | 85-86-9 |
| 27290 (2) | Acid Red 73 | 5413-75-2 |
| 27755 | E152 ; Food Black 2 | 2118-39-0 |
| 28440 | E 151; Brilliant Black 1; Food Black 1; Brilliant Black BN; Black PN | 2519-30-4 |
| 40215 | Direct Orange 34 | 1325-54-8 |
| 40800 | Beta Carotene (synthetic) ; Food Orange 5 | 7235-40-7 |
| 40820 | E 160e; Food Orange 6; β-Apo-8' Carotenal (C 30) | 1107-26-2 |
| 40825 | E 160f; Food Orange 7; Ethyl Ester of β-Apo-8' Carotenic Acid (C 30) | 1109-11-1 |
| 40850 | Canthaxanthin; E 161g; Food Orange 8 | 514-78-3 |
| 42045 | Acid Blue 1 | 129-17-9 |
| 42051 (2) | E 131; Acid Blue 3; Patent Blue V | 3536-49-0 |
| 42053 | FD&C Green No. 3; Food Green 3; Fast Green FCF | 2353-45-9 |
| 42080 | Acid Blue 7 | 3486-30-4 |
| 42090 | FD&C Blue No. 1; Acid Blue 9 (Sodium salt) ; Food Blue 2; Brilliant Blue FCF; Patent Blue AC | 3844-45-9 |
| | FD&C Blue No. 4; Acid Blue 9 (Ammonium salt) ; Alphazurine FG; Erioglaucine | 6371-85-3 |
| 42100 | Acid Green 9 | 4857-81-2 |
| 42170 | Acid Green 22 | 5863-51-4 |
| 42510 | Basic Violet 14 | 632-99-5 |
| 42520 | Basic Violet 2 | 3248-91-7 |
| 42735 | Acid Blue 104 | 6505-30-2 |
| 44045 | Basic Blue 26 | 2580-56-5 |
| 44090 | E142 ; Acid Green 50; Green S | 3087-16-9 |
| 45100 | Acid Red 52 | 3520-42-1 |
| 45190 | Acid Violet 9 | 6252-76-2 |
| 45220 | Acid Red 50 | 5873-16-5 |
| 45350 | D&C Yellow No. 8; Acid Yellow 73; Uranine | 518-47-8 |
| 45350:1 | D&C Yellow No. 7; Solvent Yellow 94; Fluorescein | 2321-07-5 |
| 45370 (2) | Acid Orange 11 | |
| 45370:1 | D&C Orange No. 5; Solvent Red 72; Dibromofluorescein | 596-03-2 |
| 45380 (2) | D&C Red No. 22; Acid Red 87; Eosin Y | 17372-87-1 |
| 45380:2 | D&C Red No. 21; Solvent Red 43; Tetrabromofluorescein | 15086-94-8 |
| 45396 | Solvent Orange 16 | 24545-86-6 |
| 45405 | Acid Red 98 | 6441-77-6 |
| 45410 (2) | D&C Red No. 28; Acid Red 92; Phloxine B | 18472-87-2 |
| 45410:1 | D&C Red No. 27; Solvent Red 48; Tetrabromotetrachloro-; Fluorescein | 13473-26-2 |
| 45425 | D&C Red No. 11; Acid Red 95; Erythrosine Yellowish Na | 33239-19-9 |
| 45425:1 | D&C Orange No. 10; Solvent Red 73; Diiodofluorescein | 38577-97-8 |
| 45430 (2) | E 127; FD&C Red No. 3; Acid Red 51; Erythrosine; Food Red 14 | 16423-68-0 |
| 47000 | D&C Yellow No. 11; Solvent Yellow 33; Quinoline Yellow SS | 8003-22-3 |
| 47005 | D&C Yellow No. 10; E104; Acid Yellow; Food Yellow 13; Quinoline Yellow; Canary Yellow | 8004-92-0 |
| 50325 | Acid Violet 50 | 229-951-1 |

| | | |
|---|---|---|
| 50420 | Acid Black 2 | 8005-03-6 |
| 51319 | Pigment Violet 23 | 6358-30-1 |
| 58000 | Pigment Red 83; Alizarin | 72-48-0 |
| 59040 | D&C Green No. 8; Solvent Green 7; Pyranine Concentrated | 6358-69-6 |
| 60724 | Disperse Violet 27 | 19286-75-0 |
| 60725 | D&C Violet No. 2; Solvent Violet 13; Alizurol Purple SS | 81-48-1 |
| 60730 | Ext D&C Violet No. 2; Acid Violet 43 | 4430-18-6 |
| 61565 | D&C Green No. 6; Solvent Green 3; Quinizarin Green SS | 128-80-3 |
| 61570 | D&C Green No. 5; Acid Green 25 | 4403-90-1 |
| 61585 | Acid Blue 80 | 4474-24-2 |
| 62045 | Acid Blue 65 | 4368-56-3 |
| 69800 | E 130; Vat Blue 4 | 81-77-6 |
| 69825 | D&C Blue No. 9; Vat Blue 6; Indanthrene Blue; Carbanthrene Blue | 130-20-1 |
| 71105 | Vat Orange 7; Pigment Orange 43 | 4424-06-0 |
| 73000 | Vat Blue 1; Indigo | 482-89-3 |
| 73015 | FD&C Blue No. 2; E 132; Food Blue 1; Indigotine; Indigo Carmine | 860-22-0 |
| 73360 | D&C Red No. 30; Vat Red 1; Helindone Pink CN | 2379-79-0 |
| 73385 | Vat Violet 2 | 5462-29-3 |
| 73900 | Pigment Violet 19 | 1047-16-1 |
| 73915 | Pigment Red 122 | 16043-40-6 |
| 74100 | Pigment Blue 16 | 547-93-6 |
| 74160 | Pigment Blue 15 | 147-14-8 |
| 74180 | Direct Blue 86 | 1330-38-7 |
| 74260 | Pigment Green 7 | 1328-53-6 |
| 75100 | Natural Yellow 6 | 27876-94-4 |
| 75120 | Annatto extract; E 160b; Natural Orange 4 | 1393-63-1 |
| 75125 | E 160d; Lycopene | 502-65-8 |
| 75130 | Beta Carotene (Natural) ; E 160a; Natural Browns 5; Natural Yellow 26 | 7235-40-7 |
| 75135 | E 161d; Natural Yellow 27; Rubixanthin | 3763-55-1 |
| 75170 | Guanine; Natural White 1 | 73-40-5 |
| 75300 | E 100; Natural Yellow 3; Turmeric Yellow; Curcumin; Indian Saffron | 458-37-7 |
| 75470 | Cochineal extract; E120; Natural Red 4; Cochineal; Carmine; Carminic Acid . . . | 1343-78-8 |
| | | 1390-65-4 |
| | | 1260-17-9 |
| 75480 | Henna | 83-72-7 |
| 75810 | E 140 & E 141; Chlorophyll; Copper complexes of chlorophyll and chlorophyllins; Potassium sodium copper; Chlorophyllin; Natural Green 3 | 11006-34-1 |
| 77000 | Aluminum Powder; E 173; Pigment Metal 1; Aluminum | 4729-90-5 |
| 77002 | Alumina; Pigment White 24 | 1332-73-6 |
| 77004 | Pigment White 19; Bentonite | 1302-78-9 |
| 77007 | Ultramarine Blue; Pigment Blue 29 | 1317-97-1 |
| | Ultramarine Red | 1345-00-2 |
| | Ultramarine Violet; Pigment Violet 15 | 12769-96-9 |
| 77013 | Ultramarine Green; Pigment Green 24 | |
| 77015 | Pigment Red 101; Pigment Red 102 | |
| 77019 | Mica; Pigment White 20 | 12001-26-2 |
| | Talc; Pigment white 26 | 14807-96-9 |
| 77120 | Pigment White 21; Pigment White 22 | 7727-43-7 |
| 77163 | Bismuth oxychloride; Pigment White 14 | 7787-59-9 |
| 77220 | Calcium carbonate; E 170; Pigment White 18 | 471-34-1 |
| 77231 | Pigment White 25; Calcium Sulfate | 7778-18-9 |
| 77288 | Chromium Oxide Greens; Pigment Green 17 | 1308-38-4 |
| 77289 | Chromium hydroxide Green; Pigment Green 18; Guignet Green; Veridian | 12001-99-9 |
| 77346 | Cobalt Blue; Pigment Blue 28 | 1345-16-0 |
| 77400 | Bronze powder; Copper powder; Pigment Metal 2 | 7440-50-8 |
| 77400 | | |
| 77480 | E 175; Gold; Pigment Metal 3 | 7740-57-5 |
| 77489 | E 172; Ferrous oxide | 1345-25-1 |
| 77491 | Ferric oxide; E 172; Pigments Red 101 & 102; Pigments Brown 6 & 7 | 1309-37-1 |
| 77492 | Hydrated Ferric oxide; E 172; Pigments Yellow 42 & 43; Pigments Brown 6 & 7 | 20344-49-4 |
| 77499 | Ferrous Ferric oxide; E 172; Pigment Black 11; Pigments Brown 6 & 7 | 1317-61-9 |
| 77510 | Ferric ferrocyanide; Pigment Blue 27; Prussian Blue | 14038-43-8 |
| 77520 | | |
| 77713 | Magnesium Carbonate; Pigment White 18 | 546-93-0 |
| 77742 | Manganese Violet; Pigment Violet 16 | 10101-66-3 |
| 77745 | Manganous Phosphate | 10124-54-6 |
| 77820 | Silver; E 174 | 7440-22-4 |
| 77891 | Titanium Dioxide; E 171; Pigment White 6 | 13463-67-7 |
| 77947 | Zinc Oxide; Pigment White 4 | 1317-13-2 |
| | Acid red 195 | 12220-24-5 |
| | Aluminum distearate | 300-92-5 |

-continued

| | | |
|---|---|---|
| Anthocyanins; E 163 | | 11029-12-2 |
| Beetroot red; E 162 | | 89957-89-1 |
| | | 7659-95-2 |
| Bismuth citrate | | |
| Bromocresol green | | 76-60-8 |
| Bromothymol blue | | 76-59-5 |
| Calcium stearate | | 1592-23-0 |
| Capsanthin, Capsorubin; E 160c; Paprika extract | | 465-42-9 |
| E 150; Natural Brown 10; Caramel | | 8028-89-5 |
| Ferric ammonium ferrocyanide | | 25869-00-5 |
| E 101; Lactoflavin; Riboflavin | | 83-88-5 |
| Lead acetate | | 301-04-2 |
| Magnesium Stearate | | 557-04-0 |
| Zinc Stearate | | 557-05-1 |

Table 1b: Structure of the Lakes:

| Lakes (FDA name) | Cl No | name | structure of corresponding dye |
|---|---|---|---|
| D&C Red #6 Ba Lake | 15850 | Pigment Red 57 Sodium Salt | 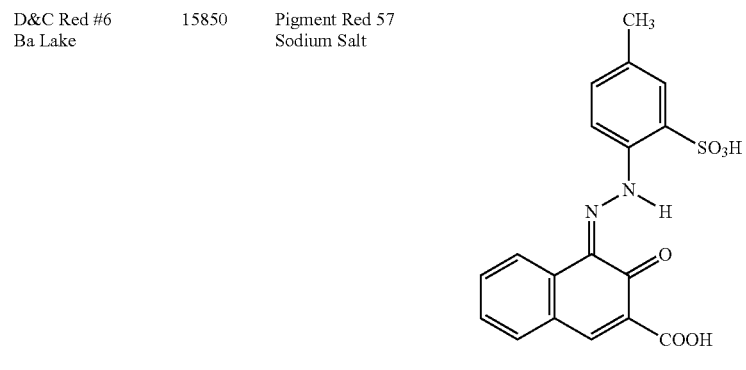 |
| D&C Red #7 | 15850:1 | Pigment Red 57.1 Calcium Salt | 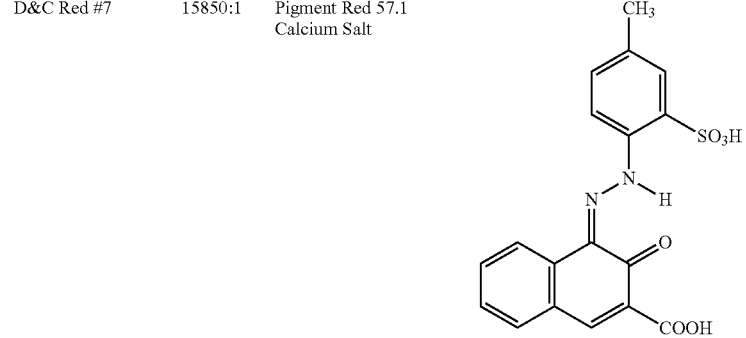 |
| D&C Red #21 Al Lake | 45380:2 | Solvent Red 43 | 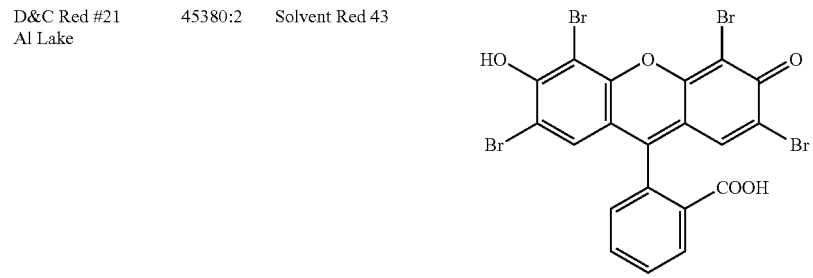 |

-continued
| | | | |
|---|---|---|---|
| D&C Red #22 Al Lake | 45380 | Acid Red 87 | 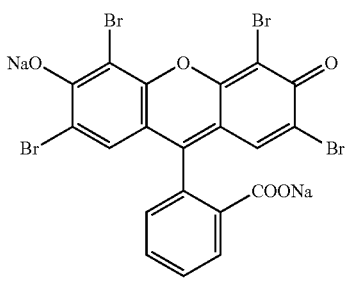 |
| D&C Red #27 Al Lake | 45410:1 | Solvent Red 48 | 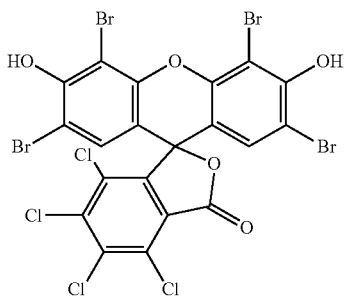 |
| D&C Red #28 Al Lake | 45410 | Acid Red 92 | 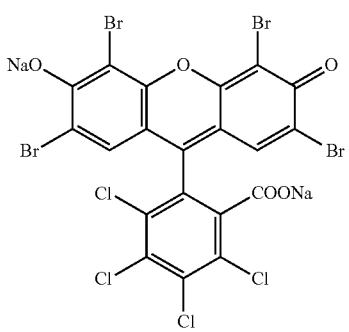 |
| D&C Red #30 Al & Talk Lake | 73360 | Vat Red 1 = Pigment Red 181 | 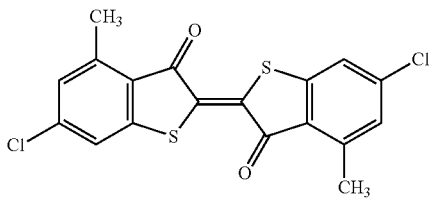 |
| D&C Red #33 Al & Zr Lake | 17200 | Acid Red 33 | 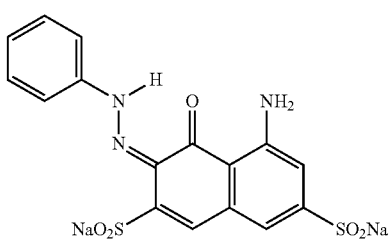 |
| D&C Yellow #10 Al Lake | 47005 | Food Yellow 13 | 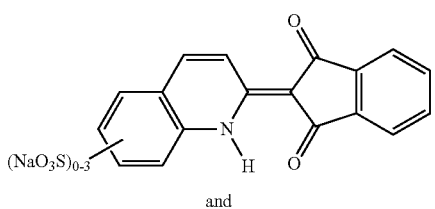 |
and -continued

| | | | |
|---|---|---|---|
| FD&C Yellow #5 Al Lake | 19140 | Acid Yellow 23 Na Salt | 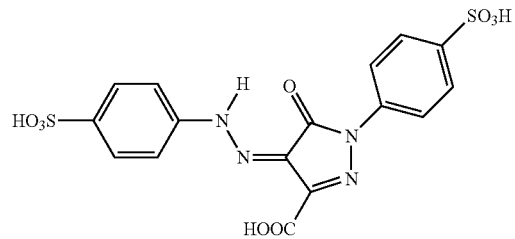 |
| FD&C Yellow #6 Al Lake | 15985 | Food Yellow 3 Na Salt | 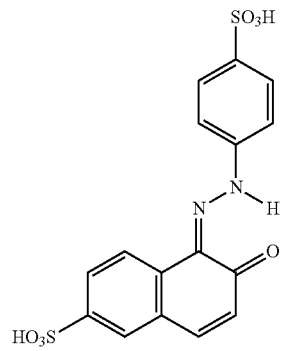 |
| FD&C Blue #1 Al Lake | 42090 | Acid blue 9 | |

| Table 1c: Calisha colour pigments (Ciba): | |
|---|---|
| Treated Pearls | |
| Name | INCI Name |
| Calisha Romance Silver Pearl OD | Mica and Titanium Dioxide and Cetyl Dimethicone |
| Calisha Romance Glamour Violet OD | Mica and Titanium Dioxide and Cetyl Dimethicone |
| Calisha Romance Glamour Blue Pearl OD | Mica and Titanium Dioxide and Cetyl Dimethicone |
| Calisha Romance Glamour Green OD | Mica and Titanium Dioxide and Cetyl Dimethicone |
| Calisha Romance Gold Pearl OD | Mica and Titanium Dioxide and Red Iron Oxide and Cetyl Dimethicone |
| Calisha Romance Bronze Pearl OD | Mica and Red Iron Oxide and Cetyl Dimethicone |
| Calisha Romance Orange Pearl OD | Mica and Red Iron Oxide and Cetyl Dimethicone |
| Calisha Romance Red Pearl OD | Mica and Red Iron Oxide and Cetyl Dimethicone |
| Calisha Contemporary Starlight Pearl OD | Mica and Titanium Dioxide and Cetyl Dimethicone |
| Calisha Contemporary Glamour Blue Pearl OD | Mica and Titanium Dioxide and Cetyl Dimethicone |
| Calisha Contemporary Glamour Gold Pearl OD | Mica and Titanium Dioxide and Cetyl Dimethicone |
| Calisha Contemporary Glamour Violet OD | Mica and Titanium Dioxide and Cetyl Dimethicone |
| Calisha Contemporary Claret Pearl OD | Mica and Red Iron Oxide and Titanium Dioxide and Cetyl Dimethicone |
| Calisha Contemporary Sienna Pearl OD | Mica and Red Iron Oxide and Titanium Dioxide and Cetyl Dimethicone |
| Calisha Contemporary Black Pearl OD | Mica and Titanium Dioxide and Black Iron Oxide and Cetyl Dimethicone |
| Calisha Contemporary Sable Pearl OD | Mica and Titanium Dioxide and and Red Iron Oxide Carmine and Cetyl Dimethicone |
| Calisha Contemporary Green Pearl OD | Mica and Titanium Dioxide and Red Iron Oxide and Ferric Ferrocyanide and Cetyl Dimethicone |
| Calisha Contemporary Silver Pearl OD | Mica and Titanium Dioxide and Cetyl Dimethicone |
| Calisha Contemporary Glamour Green OD | Mica and Titanium Dioxide and Tin Dioxide and Cetyl Dimethicone |
| Calisha Contemporary Gold Pearl OD | Mica and Titanium Dioxide and Red Iron Oxide and Cetyl Dimethicone |
| Calisha Contemporary Bronze Pearl OD | Mica and Red Iron Oxide and Cetyl Dimethicone |

-continued

| | |
|---|---|
| Calisha Contemporary Rose Red Pearl OD | Mica and Red Iron Oxide and Cetyl Dimethicone |
| Calisha Art Deco Silver Pearl OD | Mica and Titanium Dioxide and Cetyl Dimethicone |
| Calisha Art Deco Glamour Violet OD | Mica and Titanium Dioxide and Cetyl Dimethicone |
| Calisha Art Deco Glamour Blue Pearl OD | Mica and Titanium Dioxide and Cetyl Dimethicone |
| Calisha Art Deco Glamour Green OD | Mica and Titanium Dioxide and Cetyl Dimethicone |
| Calisha Art Deco Gold Pearl OD | Mica and Red Iron Oxide and Titanium Dioxide and Cetyl Dimethicone |
| Calisha Art Deco Bronze Pearl OD | Mica and Red Iron Oxide and Cetyl Dimethicone |
| Calisha Art Deco Orange Pearl OD | Mica and Red Iron Oxide and Cetyl Dimethicone |
| Calisha Art Deco Red Pearl OD | Mica and Red Iron Oxide and Cetyl Dimethicone |
| Untreated Pearls | |
| Calisha Romance Silver Pearl CL | Mica and Titanium Dioxide |
| Calisha Romance Glamour Violet CL | Mica and Titanium Dioxide |
| Calisha Romance Glamour Blue Pearl CL | Mica and Titanium Dioxide |
| Calisha Romance Glamour Green CL | Mica and Titanium Dioxide |
| Calisha Romance Gold Pearl CL | Mica and Titanium Dioxide and Red Iron Oxide |
| Calisha Romance Bronze Pearl CL | Mica and Red Iron Oxide |
| Calisha Romance Orange Pearl CL | Mica and Red Iron Oxide |
| Calisha Romance Red Pearl CL | Mica and Red Iron Oxide |
| Calisha Contemporary Starlight Pearl CL | Mica and Titanium Dioxide |
| Calisha Contemporary Glamour Blue Pearl CL | Mica and Titanium Dioxide |
| Calisha Contemporary Glamour Gold Pearl CL | Mica and Titanium Dioxide |
| Calisha Contemporary Glamour Violet CL | Mica and Titanium Dioxide |
| Calisha Contemporary Claret Pearl CL | Mica and Red Iron Oxide and Titanium Dioxide |
| Calisha Contemporary Sienna Pearl CL | Mica and Red Iron Oxide and Titanium Dioxide |
| Calisha Contemporary Black Pearl CL | Mica and Titanium Dioxide and Black Iron Oxide |
| Calisha Contemporary Sable Pearl CL | Mica and Titanium Dioxide and Red Iron Oxide and Carmine |
| Calisha Contemporary Green Pearl CL | Mica and Titanium Dioxide Red Iron Oxide Ferric Ferrocyanide |
| Calisha Contemporary Silver Pearl CL | Mica and Titanium Dioxide |
| Calisha Contemporary Glamour Green CL | Mica and Titanium Dioxide and Tin Dioxide |
| Calisha Contemporary Gold Pearl CL | Mica and Titanium Dioxide and Red Iron Oxide |
| Calisha Contemporary Bronze Pearl CL | Mica and Red Iron Oxide |
| Calisha Contemporary Rose Red Pearl CL | Mica and Red Iron Oxide |
| Calisha Art Deco Silver Pearl CL | Mica and Titanium Dioxide |
| Calisha Art Deco Glamour Violet CL | Mica and Titanium Dioxide |
| Calisha Art Deco Glamour Blue Pearl CL | Mica and Titanium Dioxide |
| Calisha Art Deco Glamour Green Pearl CL | Mica and Titanium Dioxide |
| Calisha Art Deco Gold Pearl CL | Mica and Red Iron Oxide and Titanium Dioxide |
| Calisha Art Deco Bronze Pearl CL | Mica and Red Iron Oxide |
| Calisha Art Deco Orange Pearl CL | Mica and Red Iron Oxide |
| Calisha Art Deco Red Pearl CL | Mica and Red Iron Oxide |
| Inorganic Pigments | |
| Calisha Contemporary Salmon Red Oxide | Red Iron Oxide |
| Calisha Contemporary Medium Red Oxide | Red Iron Oxide |
| Calisha Contemporary Deep Red Oxide | Red Iron Oxide |
| Calisha Contemporary Black Oxide | Black Iron Oxide |
| Calisha Contemporary Jet Black Oxide | Black Iron Oxide |
| Calisha Contemporary Sun Yellow Oxide | Yellow Iron Oxide |
| Calisha Contemporary Yellow Oxide | Yellow Iron Oxide |
| Calisha Contemporary Ultramarine Blue | Ultramarine Blue |
| Calisha Contemporary Ultramarine Violet | Ultramarine Violet |
| Calisha Art Deco Hydroxide Chrome Green | Chromium Hydroxide Green |
| Calisha Art Deco Chrome Oxide Green | Chromium Oxide Greens |
| Lakes | |
| Calisha Art Deco Blue 1 Lake | FD&C Blue No. 1 Al Lake |
| Calisha Art Deco Red 21 Lake | D&C Red No. 21 Al Lake |
| Calisha Art Deco Red 27 Lake | D&C Red No. 27 Al Lake |
| Calisha Art Deco Red 30 AL. Lake | D&C Red No. 30 Al Lake |
| Calisha Art Deco Red 30 Talc Lake | D&C Red No. 30 Talc Lake |
| Calisha Art Deco Red 33 Lake | D&C red No. 33 Al Lake |
| Calisha Art Deco Red 40 AL. Lake | FD&C Red No. 40 Al lake |
| Calisha Art Deco Red 6 Lake HD | D&C Red No. 6 Ba Lake |

-continued

| | |
|---|---|
| Calisha Art Deco Red 7 Lake HD | D&C Red No. 7 Ca lake |
| Calisha Art Deco Yellow 5 Lake HD | FD&C Yellow No. 5 Al Lake |
| Calisha Art Deco Yellow 6 AL. Lake | FD&C Yellow No. 6 Al lake |

The interference pigments as used in the present invention are platelet particulates. The platelet particulates preferably have a thickness of no more than about 5 micrometers, more preferably no more than about 2 micrometers, still more preferably no more than about 1 micrometer. The platelet particulates preferably have a thickness of at least about 0.02 micrometers, more preferably at least about 0.05 micrometers, even more preferably at least about 0.1 micrometers, and still more preferably at least about 0.2 micrometers.

Furthermore, the hair dye composition according to the present invention may also be used in combination with oxidation dye systems.

Oxidation dyes, which, in the initial state, are not dyes but dye precursors are classified according to their chemical properties into developer and coupler compounds.

Suitable oxidation dyes are described for example in
DE 19 959 479, especially in col 2, l. 6 to col 3, l. 11;
"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes).

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives or 2,4,5,6-tetraminopyrimidine derivatives.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

Preferred coupler compounds are m-phenylenediamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

Furthermore, autooxidizable compounds may be used in combination with the hair dye composition according to the present invention.

Autooxidizable compounds are aromatic compounds with more than two substituents in the aromatic ring, which have a very low redox potential and will therefore be oxidized when exposed to the air. The dyeings obtained with these compounds are very stable and resistant to shampoo.

Autooxidizable compounds are for example benzene, indole, or indole, especially 5,6-dihydroxyindol or 5,6-dihydroxyindol.

The hair dye composition according to the present invention may also be used in combination with naturally occurring dyes, such as henna red, henna neutral, henna black, camomile blossom, sandalwood, black tea, *Rhamnus frangula* bark, sage, campeche wood, madder root, catechu, sedre and alkanet root.

Furthermore, the hair dye composition according to the present invention may also be used in combination with capped diazotized compounds.

Suitable diazotized compounds are for example the compounds of formulae (1)-(4) in WO 2004/019897 (bridging gages 1 and 2) and the corresponding water-soluble coupling components (I)-(IV) as disclosed in the same reference.

The present invention also relates to formulations, which are used for the dyeing of organic materials, preferably keratin-containing fibers, and most preferably human hair, comprising the hair dye composition according to the present invention.

The appropriate dyeing medium (or carrier) generally consists of water or of a mixture of water and of at least one organic solvent for solubilizing the compounds which would not be sufficiently soluble in water. As organic solvent, there may be mentioned for example the $C_1$-$C_4$ lower alkanols such as ethanol and isopropanol, the aromatic alcohols such as benzyl alcohol as well as similar products and mixtures thereof.

The solvents may be present in proportions preferably of between 1 and 40% by weight approximately relative to the total weight of the dyeing composition, and still more preferably between 5 and 30% by weight approximately.

Preferably the hair dye composition according to the present invention is incorporated into the composition for treating organic material, preferably for dyeing in amounts of 0.001-5% b.w. (hereinafter indicated merely by "%"), particularly 0.005-4%, more particularly 0.2-3%, based on the total weight of the composition.

The pH of the dyeing composition in accordance with the invention is generally between 2 and 11 approximately, and preferably between 5 and 10 approximately. It may be adjusted to the desired value by means of acidifying or alkalinizing agents normally used in dyeing keratinous fibres.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

One preferred embodiment of the present invention relates to the formulation of dyes, wherein the hair dye composition according to the present invention is in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts, for example emulsifiers may be present in the dyeing compositions in concentrations of from 0.5 to 30% b.w. and thickeners in concentrations of from 0.1 to 25% b.w. of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

The hair dye composition according to the present invention may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

The dyeing compositions according to the invention may comprise any active ingredients, additives or adjuvants known for such preparations, like surfactants, solvents, bases, acids, perfumes, polymeric adjuvants, thickeners and light stabilizers.

The following adjuvants are preferably used in the hair dyeing compositions of the present invention: non-ionic polymers, cationic polymers, acrylamide/dimethyldiallylammonium chloride copolymers, quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilizers, anti-dandruff active ingredients, substances for adjusting the pH value; panthenol, pantothenic acid, allantoin, pyrrolidonecarboxylic acids and salts thereof, plant extracts and vitamins; cholesterol; light stabilizers and UV absorbers, consistency regulators, fats and waxes, fatty alkanol-amides, polyethylene glycols and polypropylene glycols, complexing agents, swelling and penetration substances, opacifiers, such as latex; pearlising agents, propellants, antioxidants; sugar-containing polymers, quaternary ammonium salts, or bacteria inhibiting agents.

The dyeing compositions according to the present invention generally comprise at least one surfactant. Suitable surfactants are zwitterionic or ampholytic, or more preferably anionic, non-ionic and/or cationic surfactants.

Suitable anionic surfactants are characterized by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$-carboxylic acids, such as oleic acid, stearic acid, isostearic acid and palmitic acid.

Surface-active compounds that carry at least one quaternary ammonium group and at least one —COO⁻ or —SO₃⁻ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazol. having from 8 to 18 carbon atoms in the alkyl or acyl group and also cocoacylaminoethylhydroxyethylcarboxymethyl glycinate. A preferred zwitter-ionic surfactant is the fatty acid amide derivative known by the CTFA name cocamidopropyl betaine.

Ampholytic surfactants are surface-active compounds that, in addition to a $C_8$-$C_{18}$-alkyl or -acyl group and contain at least one free amino group and at least one —COOH or —SO₃H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, l. 11 to p. 50, l. 12. Non-ionic surfactants contain as hydrophilic group, for example, a polyol group, a polyalkylene glycol ether group or a combination of polyol and polyglycol ether groups.

Examples of cationic surfactants that can be used in the dyeing compositions according to the invention are especially quaternary ammonium compounds.

Alkylamidoamines, especially fatty acid amidoamines, such as the stearylamidopropyldi-methylamine obtainable under the name Tego Amid® 18 are also preferred as surfactants in the present dyeing compositions. They are distinguished not only by a good conditioning action but also especially by their good biodegradability.

A further preferred embodiment of the present invention relates to a method of treating keratin-containing fibers with the hair dye composition according to the present invention.

The method comprises treating the hair in the presence of a reduction agent.

Usually, the dyeing compositions are applied to the keratin-containing fiber in an amount of from 50 to 100 g.

The oxidizing agents described above can also be used as lightening composition for lightening of the hair before the intrinsic dyeing process.

Therefore, the present invention also relates to a method for simultaneous dyeing and waving of keratinous fibers, comprising the steps of (a) treating the hair with a lightening composition,
(b) optionally treating the hair with a reductive wave agent; and
(c) treating the hair with a hair dyeing composition according to the present invention.

Moreover, this method is also suitable for the smoothing of hair.

The hair dye composition according to the present invention is suitable for all-over dyeing of the hair, that is to say when dyeing the hair on a first occasion, and also for redyeing subsequently, or dyeing of locks or parts of the hair, for example for the dyeing of eyebrows, eyelashes, body hair and or beards.

The hair dye composition according to the present invention is applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with the hair dye composition according to the present invention, a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

In general, the oxidizing agent containing composition is left on the fiber for 0 to 15 minutes, in particular for 0 to 5 minutes at 15 to 45° C., usually in amounts of 30 to 200 g.

Oxidizing agents are for example persulfate or diluted hydrogen peroxide solutions, hydrogen peroxide emulsions or hydrogen peroxide gels, alkaline earth metal peroxides, organic per-oxides, such as urea peroxides, melamine peroxides, or alkalimetalbromate fixations are also applicable if a shading powder on the basis of semi-permanent, direct hair dyes is used.

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula $$\begin{array}{c} R_3 \\ \diagdown \\ N-R-N \\ \diagup \\ R_4 \end{array} \begin{array}{c} R_5 \\ \diagup \\ \diagdown \\ R_6, \end{array}$$

wherein
R is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the hair dye composition according to the present invention on the keratin-containing fiber, preferably the hair is by using a multi-compartment dyeing device or "kit" or any other multi-compartment packaging system, as described for example in WO 97/20545 on p. 4, l. 19 to l. 27.

The following Examples serve to illustrate the processes for dyeing without limiting the processes thereto. Unless specified otherwise, parts and percentages relate to weight. The amounts of dye specified are relative to the material being colored.

APPLICATION EXAMPLES

1. Combination of Basic Blue 124 with Basic Red 76, Basic Yellow 57, Basic Brown 16, Basic Brown 17 and Basic Blue 99 for dyeing of hair
2. Combination of Basic Blue 124 with Basic Red 76, Basic Yellow 57, Basic Brown 16, Basic Brown 17 and Basic Blue 99 and Basic Red 51, Basic Yellow 87 and Basic Orange 31 for dyeing hair For the application examples the following hair types have been used:
1 blonde hair tress (VIRGIN White Hair),
1 middle blonde hair tress (UNA-Europ. nature hair, Color middle blonde),
1 bleached hair tress (UNA-Europ. nature hair, Color white bleached).

Coloring Solution:
0.1% w/w of the dye is dissolved in a Plantaren solution (5% w/w Plantacare 2000UP (ID: 185971.5) in water; pH adjusted to 9.5 with 50% citric acid solution or monoethanolamine solution).

The hair tresses were dyed according to the following procedure:

The coloring solution was applied directly to the dry hair, incubated for 20 min. at room temperature, and then rinsed off under tap water (Water temperature: 37° C.+/−1° C.; flow rate of water: 5-6 l/min.). Then it was pressed out with a paper towel and dried over night at room temperature on a glass plate.

To determine the wash fastness two sets of hair tresses were dyed under the same conditions. One set of the dyed tresses was washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min). Finally the tresses were rinsed under tap water, pressed out with a paper towel, combed and dried with a hair dryer or at room temperature. This procedure was repeated 10 times.

Then the color loss of the set of washed tresses relative to the set of unwashed tresses was evaluated using the Grey Scale according to: Industrial Organic Pigments by Herbst&Hunger, 2nd ed., p. 61, Nr 10: DIN 54 001-8-1982, "Herstellung and Bewertung der Änderung der Farbe", ISO 105-A02-1993.

Example 1

0.1% of Basic Blue 124 is dissolved in a 5% solution of a non-ionic surfactant (Plantacare 2000 UP, Henkel) adjusted to pH 9.5 using citric acid or monoethanolamine. This blue dyeing solution is applied on the dry hair (two blond, two middle blond and two damaged hair strands) and allowed to stand for 20 min at room temperature. Then, the strands are rinsed under tap water and dried 12 h.

Results:

| Hair Type | Color | Intensity | Brilliance | Washing Fastness |
|---|---|---|---|---|
| Blond | Blue | good | good | 2-3 |
| Middle blond | Blue | good | good | 3 |
| Damaged | Blue | good | good | 2-3 |

Example 2

A dye emulsion, pH=10.5

| INGREDIENT | w/w % |
|---|---|
| Basic Blue 124 | 1 |
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Deionized Water 70° C. | ad 100.0 | is mixed with 1.5 weight of 9% hydrogen peroxide solution and the mixture is immediately applied to a tress of brown hair. After 30 minutes the tress is rinsed, shampooed, rinsed and dried. The tress has been dyed blue.

Results:

| Hair Type | Color | Intensity | Brilliance | Washing Fastness |
|---|---|---|---|---|
| Blond | Blue | good | good | 3-4 |
| Middle blond | Blue | good | good | 3 |
| Damaged | Blue | good | good | 2-3 |

Example 3

A dye emulsion, containing 1% of the dye pH=9.8

| Basic Blue 124 | 0.25 |
|---|---|
| Basic Blue 151 | 0.25 |
| Basic Red 51 | 0.25 |
| Basic Red 76 | 0.25 |
| Acid Red 52 | 0.01 |
| Cetylstearylalcohol | 11.00 |
| Oleth-5 | 5.0 |
| Oleic acid | 2.5 |
| Stearic acid monoethanolamide | 2.5 |
| Coco fatty acid monoethanolamide | 2.5 |
| Sodium laurylsulphate | 1.7 |
| 1,2-Propanediol | 1.0 |
| Ammonium chloride | 0.5 |
| EDTA, Tetrasodium salt | 0.2 |
| Perfume | 0.4 |
| Cornproteinhydrolysate | 0.2 |
| Silica | 0.1 | is mixed with the same weight of 6% hydrogen peroxide solution and the mixture is immediately applied to a tress of brown hair. After 30 minutes the tress is rinsed, shampooed, rinsed and dried. The tress has been dyed violet.

Example 4

A dye emulsion with pH=6.4, containing
0.05% of the dye Basic Blue 124
0.15% Basic Blue 99
0.07% Basic Brown 17
0.04% Basic Yellow 57
0.15% Basic Brown 16
0.01% Basic Red 76
0.01% Basic Red 51
0.01% HC Red BN
0.01% HC Red 3
0.01% 3-Nitro-p-Hydroxyethylaminophenol
0.05% HC Blue 2
3.5% Cetearyl alcohol
1.0% Ceteareth 30
0.5% Glycol Distearate
3.0% Stearamide DEA
1.0% Sodium Oleoamphohydroxypropyl Sulfonate
0.5% Polyquarternium-6
0.1% Tinovis CD (Dimethylacrylamide/Ethyltrimonium Chloride Methacrylate Copolymer, Propylene Glycol Dicaprylate/Dicaprate, PPG-1 Trideceth-6, C10-11 Isoparaffin) water ad 100%
is applied for 30 minutes, at room temperature to bleached human hair, and rinsed. The result is a reddish brown dyeing with good fastnesses.

Example 5

A dye emulsion containing

| Cetearyl Alcohol | 12.000 |
|---|---|
| Ceteareth-25 | 5.000 |
| Glyceryl Stearate SE | 2.500 |
| Glycol Distearate | 0.500 |
| Oleth-10 | 2.000 |
| Cetearyl Ethylhexanoate | 0.750 |
| Deionized Water 70° C. | Ad 100 |
| Disodium EDTA | 0.050 |
| Basic Blue 124 | 0.800 |
| Basic Red 51 | 0.100 |
| Monoethanolamine 99% | 1 dro |
| Hydrolyzed Wheat Protein 20% | 1.000 |
| Monoethanolamine 99% | ~0.900 |
| Fragrance Drom 854 148 Linden Blossom | 0.500 |
| pH-Value: 6.02 | | is applied for 30 minutes, at room temperature, to colored middle blond human hair, and rinsed. The result is a reddish blue dyeing with good fastnesses.

Example 6

60 ml of part A, 60 ml of part B and 3 ml of part C are mixed in a mixing bowl or applicator bottle and the mixture is immediately applied to a tress of brown hair. After 30 minutes the tress is rinsed, shampooed, rinsed and dried. The tress has been dyed an intensive violet.

| | Shade: Pure Red INGREDIENT | w/w % |
|---|---|---|
| Part A | Deionized Water RT | 20.00 |
| | Sodium Sulfite | 0.60 |
| | Disodium EDTA | 0.05 |
| | Cocamidopropyl Betaine 30% | 4.00 |
| | Propylene Glycol | 2.50 |
| | Monoethanolamine 99% | 1.00 |
| | Toluene-2,5-Diamine Sulfate | 0.25 |
| | p-Aminophenol | 0.50 |
| | 4-Amino-2-Hydroxytoluene | 0.70 |
| | 2-Methyl-5-Hydroxyethylaminophenol | 0.50 |
| | 2-Amino-4-Hydroxyethyl AA Sulfate | 0.10 |
| | Erythorbic Acid | 0.40 |
| | Deionized Water RT | 43.55 |
| | Hydroxyethylcellulose - Natrosol 250 HHR CG | 0.75 |
| | Deionized Water RT | 10.00 |
| | Isopropyl Alcohol | 8.00 |
| | Oleth-10 | 1.00 |
| | Oleic Acid | 1.10 |
| | Lactamide MEA | 1.00 |
| | Fragrance Drom 837 375 Tropical Fever | 0.50 |
| | Dihydroxypropyl PEG-5 Linoleammonium Chloride | 0.50 |
| | Hydrolyzed Soy Protein | 0.50 |
| | Monoethanolamine 99% | ~2.50 |
| | Total: | 100.00 |
| Part B: Developer 6% | Deionized Water RT | 80.50 |
| | Disodium Phosphate | 0.15 |
| | Salcare SC80 | 5.00 |
| | Glycerin 99% | 1.00 |
| | Sodium Laureth Sulfate 27% | 1.00 |
| | Etidronic Acid 60% | ~0.35 |
| | Hydrogen Peroxide 50% | 12.00 |
| | Total: | 100.00 |
| Part C | Deionized Water RT | 99.00 |
| | Basic Blue 124 | 1.00 |
| | Total: | 100.00 |

Example 7

60 ml of part A, 60 ml of part B and 3 ml of part C are mixed in a mixing bowl or applicator bottle and the mixture is immediately applied to a tress of brown hair. After 30 minutes the tress is rinsed, shampooed, rinsed and dried. The tress has been dyed an intensive black.

| | Shade: Black INGREDIENT | w/w % |
|---|---|---|
| Part A | Deionized Water RT | 20.00 |
| | Sodium Sulfite | 0.60 |
| | Disodium EDTA | 0.05 |
| | Cocamidopropyl Betaine 30% | 4.00 |
| | Propylene Glycol | 2.50 |
| | Monoethanolamine 99% | 1.00 |
| | Toluene-2,5-Diamine Sulfate | 3.00 |
| | Resorcine | 0.80 |
| | 3-Aminophenol | 0.40 |
| | 2,4-Diaminophenoxyethanol HCL | 0.80 |
| | Erythorbic Acid | 0.40 |
| | Deionized Water RT | 43.55 |
| | Hydroxyethylcellulose - Natrosol 250 HHR CG | 0.75 |
| | Deionized Water RT | 10.00 |
| | Isopropyl Alcohol | 8.00 |
| | Oleth-10 | 1.00 |
| | Oleic Acid | 1.10 |
| | Lactamide MEA | 1.00 |
| | Fragrance Drom 837 375 Tropical Fever | 0.50 |
| | Dihydroxypropyl PEG-5 Linoleammonium Chloride | 0.50 |
| | Hydrolyzed Soy Protein | 0.50 |
| | Monoethanolamine 99% | ~2.50 |
| | Total: | 100.00 |
| Part B: Developer 6% | Deionized Water RT | 80.50 |
| | Disodium Phosphate | 0.15 |
| | Salcare SC80 | 5.00 |
| | Glycerin 99% | 1.00 |
| | Sodium Laureth Sulfate 27% | 1.00 |
| | Etidronic Acid 60% | ~0.35 |
| | Hydrogen Peroxide 50% | 12.00 |
| | Total: | 100.00 |
| Part C | Deionized Water RT | 99.00 |
| | Basic Blue 124 | 1.00 |
| | Total: | 100.00 |

Example 8

A dye emulsion, containing 1% of Basic Blue 124 pH=10.5

| INGREDIENT | w/w % |
|---|---|
| Cetearyl Alcohol | 12.00 |
| Ceteareth-20 | 4.50 |
| Polysorbate 60 | 2.3 |
| Glyceryl Stearate SE | 2.00 |
| Sorbitan Stearate | 0.75 |
| Oleth-5 | 1.25 |
| Caprylic/Capric Triglyceride | 0.50 |
| Deionized Water 70° C. | 66.65 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Total: | 100.00 | is mixed with 1.5 weight of 9% hydrogen peroxide solution and the mixture is immediately applied to a tress of brown hair. After 30 minutes the tress is rinsed, shampooed, rinsed and dried. The tress has been dyed an intensive blue.

Example 9

A dye emulsion, containing
0.1% Basic Blue 124 and

| INGREDIENT | w/w % |
|---|---|
| Deionized Water RT | 64.68 |
| Acrylates/C10-30 Alkyl Acrylate Crosspolymer | 0.55 |
| Sodium Hydroxide 25% | 0.03 |
| DMDM Hydantoin | 0.50 |
| Sodium Cocoamphoacetate 32% | 15.00 |
| Ococamidopropyl Betaine 30% | 3.00 |
| Decyl Glucoside | 3.00 |

| INGREDIENT | w/w % |
| --- | --- |
| Polyquaternium-7 | 0.50 |
| PEG-15 Copolyamine | 0.50 |
| PEG-75 Lanolin | 0.50 |
| Deionized Water RT | 10.00 |
| Disodium EDTA | 0.05 |
| Basic Red 76 | 0.1 |
| Basic Yellow 57 | 0.1 |
| Basic Blue 124 | 0.1 |
| PEG-40 Hydrogenated Castor Oil | 0.95 |
| Fragrance Drom 837 375 Tropical Fever | 0.45 |
| Citric Acid 25% Solution | ~0.20 |
| Total: | 100.00 | is applied for 30 min, at room temperature, to blond human hair, and rinsed.

The result is a very attractive vibrant violet dyeing with good fastnesses.

Example 10

A tress of gray hair is shampooed with a shampoo, containing
0.01% of Basic Blue 124 and

| INGREDIENT | w/w % |
| --- | --- |
| Disodium PEG-5 Laurylcitrate Sulfosuccinate, Sodium Laureth Sulfate | 8.25% |
| Sodium Cocoamphoacetate | 20.9% |
| Methoxy PEG/PPG-7/3 Aminopropyl Dimethicone | 0.5% |
| Hydroxypropyl Guar hydroxypropyltrimonium Chloride | 0.3% |
| PEG-200 Hydrogenated Glyceryl Palmate; PEG-7 Glyceryl Cocoate | 2.5% |
| PEG-150 Distearate | 0.5% |
| Citric Acid (30%) | 2.2% |
| Perfume; Preservatives | q.s. |
| Water | Ad 100% |

After 5 minutes the tress is rinsed and dried. The tress has been more brilliant less yellowish.

Example 11

A tress of gray hair is shampooed with a shampoo, containing

| INGREDIENT | w/w % |
| --- | --- |
| Disodium PEG-5 Laurylcitrate Sulfosuccinate, Sodium Laureth Sulfate | 8.25% |
| Sodium Cocoamphoacetate | 20.9% |
| Methoxy PEG/PPG-7/3 Aminopropyl Dimethicone | 0.5% |
| Hydroxypropyl Guar hydroxypropyltrimonium Chloride | 0.3% |
| PEG-200 Hydrogenated Glyceryl Palmate; PEG-7 Glyceryl Cocoate | 4.0% |
| PEG-150 Distearate | 0.5% |
| Basic Blue 124 | 0.01 |
| Basic Red 76 | 0.05 |
| Citric Acid (30%) | 2.2% |
| Perfume; Preservatives | q.s. |
| Water | Ad 100% |

The tress has been more brilliant violet.

Example 12

A tress of gray hair is shampooed with a shampoo, containing

| INGREDIENT | w/w % |
| --- | --- |
| Water | 87.5 |
| Hydroxyethylcellulose | 2.5 |
| Plantacare 50% | 10.0 |
| Sodium hydroxide 50% | 0.17 |
| Sodium hydroxide 0.1M | 0.77 |
| Basic Red 51 | 0.015 |
| Basic Blue 124 | 0.013 |
| Basic Yellow 87 | 0.06 |
| Citric Acid (50%) | 0.35 |
| Perfume; Preservatives | q.s. |
| pH Approx. 6.0 | |

The tress has been dyed middle brown with a medium gray coverage.

Example 13

A conditioner containing

| INGREDIENT | w/w % |
| --- | --- |
| Cetyl Alcohol | 3.00% |
| Ceterareth-25 | 0.50% |
| Distearyldimonium Chloride | 1.00% |
| Quaternium-80 | 0.50% |
| Citric Acid | Ad pH = 5 |
| Basic Blue 124 | 0.025 |
| Basic Yellow 87 | 0.060 |
| Basic Red 51 | 0.015 |
| Perfumes; Preservatives | q.s. |
| Water | Ad 100% | is applied to a tress of shampooed middle blond and gray hair. After 15 min the tress is rinsed and dried.

The tress has been dyed brown with good gray coverage.

Example 14

A conditioner containing

| INGREDIENT | w/w % |
| --- | --- |
| Cetyl Alcohol | 3.00% |
| Ceterareth-20 | 0.50% |
| Hydroxypropyl Guar, Hydroxypropyltrimonium chloride | 1.00% |
| Quaternium-80 | 0.50% |
| Citric Acid | Ad pH = 5 |
| Octocrylene | 0.1 |
| Butyl Methoxybibenzoylmethane | 0.1 |
| Perfumes; Preservatives | q.s. |
| Basic Blue 124 | 0.1 |
| Water | Ad 100% | is applied to a tress of shampooed blond hair. After 5 min the tress is rinsed and dried. The tress has been dyed blue.

Example 15

A conditioner containing

| INGREDIENT | w/w % |
| --- | --- |
| Cetearyl Alcohol, Sodium Cetearyl Sulfate | 3.00% |
| Ceterareth-25 | 0.50% |
| Distearoylethyl Diammonium Chloride | 1.00% |
| Quaternium-80 | 0.50% |
| Citric Acid | Ad pH = 5 |
| Camphor Benzalkonium Methosulfate | 0.1 |
| Ethyl Salicylate | 0.1 |
| Basic Blue 124 | 0.5 |
| Basic Red 76 | 0.5 |
| Perfumes; Preservatives | q.s. |
| Water | Ad 100% | is applied to a tress of shampooed blond hair. After 5 min the tress is rinsed and dried. The tress has been dyed violet.

Example 16

A conditioner containing

| INGREDIENT | w/w % |
| --- | --- |
| Cetyl Alcohol | 3.00% |
| Ceterareth-25 | 0.50% |
| Behentrimmonium Chloride | 1.00% |
| Quaternium-80 | 0.50% |
| Citric Acid | Ad pH = 5 |
| Dimethicone | 0.9 |
| Phenyltrimethicone, Silicone Quaternium-15, Laureth-4 (Polysil 1849) | 2.5 |
| Polysilicone-15 | 0.8 |
| Basic Blue 124 | 0.1 |
| Basic Blue 151 | 0.1 |
| Basic Blue 99 | 1.0 |
| Basic Brown 17 | 0.9 |
| Basic Yellow 57 | 0.4 |
| Basic Brown 16 | 0.9 |
| Perfumes; Preservatives | q.s. |
| Water | Ad 100% | is applied to a tress of shampooed gray hair. After 5 min the tress is rinsed and dried. The tress has been dyed dark brown.

Example 17

A dye emulsion, containing
0.05% of the dye Basic Blue 124
0.15% Basic Blue 99
0.07% Basic Brown 17
0.04% Basic Yellow 57
0.15% Basic Brown 16
0.01% Basic Red 51
0.01% Basic Orange
0.01% Basic Red 76
0.01% Basic Yellow 87
3.5% Cetearyl alcohol
1.0% Ceteareth 80
0.5% Glycol Distearate
3.0% Stearamide DEA
1.0% Sodium Oleoamphohydroxypropyl Sulfonate
0.5% Polyquarternium-6
0.2% Disodium distyrylbiphenyl disulfonate and water ad 100% is applied for 30 minutes, at room temperature to bleached human hair, and rinsed. The result is a brown dyeing with good fastnesses.

Example 18

A conditioner containing

| INGREDIENT | w/w % |
| --- | --- |
| Cetyl stearyl Alcohol | 5.0 |
| 1,2-Propandiol | 1.5 |
| Behentrimmonium Chloride | 2.0 |
| Di-C12-C15-alkyldimoniumchlorid | 1.0 |
| Cocoamidopropylbetaine | 1.0 |
| Sodium cocoamphoacetate | 0.5 |
| Henna extract | 0.5 |
| Silicon oil | 0.5 |
| Basic Blue 124 | 0.1 |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Perfumes; Preservatives | q.s. |
| Water | Ad 100% | is applied to a tress of shampooed middle blonde hair. After 5 min the tress is rinsed and dried. The tress has been dyed evenly brown.

Example 19

A conditioner containing

| INGREDIENT | w/w % |
| --- | --- |
| Hydroxyethylcellulose | 1.00 |
| Cetylstearylalcohol | 1.25 |
| 1,2-Propandiol | 3.00 |
| Cetyltrimethylamonium Chloride | 0.2 |
| Dicetyldimethylamonium Chloride | 0.30 |
| Dimethicone | 0.2 |
| Polyquaternium-10 Laurylhydroxysultain | 1.0 |
| Camoille extract | 0.5 |
| Citric acid | 0.5 |
| Basic Blue 124 | 0.1 |
| Basic Red 76 | 0.1 |
| Perfumes; Preservatives | q.s. |
| Water | Ad 100% | is applied to a tress of shampooed blonde hair. After 5 min the tress is rinsed and dried. The tress has been dyed evenly violet.

Example 20

A conditioner containing

| INGREDIENT | w/w % |
| --- | --- |
| Cetyl stearyl Alcohol | 5.0 |
| Di-C12-C15-alkyldimoniumchlorid | 2.0 |
| 1,2-Propandiol | 1.5 |
| Ceteareth-20 | 1.0 |
| Sodium cocoamphoacetate | 1.3 |
| Basic Blue 124 | 0.1 |

-continued

| INGREDIENT | w/w % |
| --- | --- |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Methylparaben | 0.2 |
| Perfume | 0.3. |
| Water | Ad 100% | is applied to a tress of shampooed middle blonde hair. After 5 min the tress is rinsed and dried. The tress has been dyed evenly brown.

Example 21

A conditioner containing

| INGREDIENT | w/w % |
| --- | --- |
| Cetyl stearyl Alcohol | 5.0 |
| Di-C12-C15-alkyldimoniumchlorid | 2.0 |
| 1,2-Propandiol | 1.5 |
| Ceteareth-20 | 1.0 |
| Sodium cocoamphoacetate | 1.3 |
| Basic Blue 124 | 0.15 |
| Basic Red 76 | 0.01 |
| Basic Brown 17 | 0.8 |
| Basic Yellow 57 | 0.3 |
| Basic Brown 16 | 0.8 |
| Methylparaben | 0.2 |
| Perfume | 0.3. |
| Water | Ad 100% | is applied to a tress of shampooed middle blonde hair. After 5 min the tress is rinsed and dried. The tress has been dyed evenly dark brown.

Example 22

A conditioner containing

| INGREDIENT | w/w % |
| --- | --- |
| Cocoamidopropylbetaine | 1.0 |
| Ceteareth-20 | 1.0 |
| Cetyl stearyl Alcohol | 1.0 |
| Dioleoylhydroxyethylmoniummethosulfate | 2.0 |
| Benzophenone-4 | 0.5 |
| Perfume | 0.2 |
| Methylparaben | 0.2 |
| Pyrrolidoncarboxylic acid | 0.1 |
| Basic Blue 124 | 0.1 |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Basic Red 51 | 0.1 |
| Basic Yellow 87 | 0.1 |
| Basic Orange 31 | 0.1 |
| Citric acid | 0.1 |
| Water | Ad 100% | is applied to a tress of shampooed middle blonde hair. After 5 min the tress is rinsed and dried. The tress has been dyed evenly brown.

Example 23

A conditioner containing

| INGREDIENT | w/w % |
| --- | --- |
| Cetyl stearyl Alcohol | 3.0 |
| Hydroxyethylcellulose | 1.00 |
| Trisodiumcarboxymethylcocopropylamine | 0.8 |
| Cetrimonium chloride | 2.0 |
| Benzophenone-9 | 0.5 |
| Panthenol | 0.1 |
| Hops extract | 0.1 |
| Basic Blue 124 | 0.1 |
| Basic Yellow 57 | 0.1 |
| Perfumes; Preservatives | q.s. |
| Water | Ad 100% | is applied to a tress of shampooed bleached hair. After 5 min the tress is rinsed and dried. The tress has been dyed evenly green.

Example 24

A foaming tint containing

| INGREDIENT | w/w % |
| --- | --- |
| Ethanol | 12.3 |
| Monoethanolamine | 0.2 |
| Octyldodecanol | 5.0 |
| Ammonium laurylsulphate | 2.0 |
| Cocamidopropyl Betaine | 12.0 |
| Disodium EDTA | 0.1 |
| Basic Blue 124 | 0.025 |
| Basic Red 51 | 0.015 |
| Basic Yellow 87 | 0.060 |
| Basic Orange 31 | 0.001 |
| Perfumes | 0.5 |
| Preservatives | q.s. |
| Water | Ad 100% |
| Propane/Butane | 10 | is applied to a tress of shampooed bleached hair. After 15 min the tress is rinsed and dried. The tress has been dyed brown.

Example 25

A setting lotion containing

| INGREDIENT | w/w % |
| --- | --- |
| Ethanol | 40.0 |
| VP/VA Copolymer | 0.4 |
| Polyquaternium-11 | 0.3 |
| Amodimethicone + Trideceth-12 + Cetrimonium Chloride | 0.5 |
| PEG-40 Hydrogenated Castor Oil | 0.2 |
| Basic Blue 124 | 0.05 |
| Perfumes | 0.5 |
| Preservatives | q.s. |
| Water | Ad 100% | is applied to a tress of shampooed gray hair. The tress has been more brilliant.

Example 26

A hair tonic containing

| INGREDIENT | w/w % |
| --- | --- |
| Ethanol | 20.0 |
| Isopropanol | 20.0 |
| PEG-40 Hydrogenated Castor Oil | 0.3 |
| Perfumes | 0.3 |
| Menthol | 0.1 |
| Coffin | 0.1 |
| *Humulus Lupulus* (Hops) Extrsct | 0.1 |
| Panthenol | 0.2 |
| Biotin | 0.1 |
| Basic Blue 124 | 0.03 |
| Water | Ad 100% | is applied to a tress of shampooed gray hair and dried. The tress has been more brilliant and less yellowish.

Example 27

A tint containing

| INGREDIENT | w/w % |
| --- | --- |
| Hydroxyethylcellulose | 2.5 |
| Plantacare 2000 50% | 10.0 |
| Ethanol | 5.0 |
| Sodium hydroxide 50% | 0.2 |
| Citric Acid 50% | 3.56 |
| Perfume | 0.2 |
| Methylparaben | 0.2 |
| Basic Blue 124 | 0.1 |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Basic Red 51 | 0.1 |
| Basic Yellow 87 | 0.1 |
| Basic Orange 31 | 0.1 |
| Citric acid | 0.1 |
| Water | Ad 100% |
| pH | 3 | is applied to a tress of shampooed middle blonde hair. After 5 min the tress is rinsed and dried. The tress has been dyed evenly brown.

Example 28

A tint containing

| INGREDIENT | w/w % |
| --- | --- |
| Hydroxyethylcellulose | 2.5 |
| Plantacare 2000 50% | 10.0 |
| Ethanol | 5.0 |
| Propylene carbonate | 25.0 |
| Sodium hydroxide 50% | 0.2 |
| Citric Acid 50% | 3.56 |
| Perfume | 0.2 |
| Methylparaben | 0.2 |
| Basic Blue 124 | 0.1 |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Basic Red 51 | 0.1 |
| Basic Yellow 87 | 0.1 |
| Basic Orange 31 | 0.1 |
| Citric acid | 0.1 |
| Water | Ad 100% |
| pH | 3 | is applied to a tress of shampooed middle blonde hair. After 5 min the tress is rinsed and dried. The tress has been dyed evenly brown.

Example 29

A tint containing

| INGREDIENT | w/w % |
| --- | --- |
| Hydroxyethylcellulose | 2.5 |
| Plantacare 2000 50% | 10.0 |
| Ethanol | 5.0 |
| Sodium hydroxide 50% | 0.2 |
| Citric Acid 50% | 3.56 |
| Perfume | 0.2 |
| Methylparaben | 0.2 |
| Basic Blue 124 | 0.1 |
| Basic Red 76 | 0.1 |
| Basic Blue 99 | 0.1 |
| Basic Brown 17 | 0.1 |
| Basic Yellow 57 | 0.1 |
| Basic Brown 16 | 0.1 |
| Basic Red 51 | 0.1 |
| Basic Yellow 87 | 0.1 |
| Basic Orange 31 | 0.1 |
| Acid Red 52 | 0.01 |
| Citric acid | 0.1 |
| Water | Ad 100% |
| pH | 3 |

Example 30

A dye emulsion with pH=6.4, containing
0.05% of the dye Basic Blue 124
0.15% Basic Blue 99
0.07% Basic Brown 17
0.04% Basic Yellow 57
0.15% Basic Brown 16
0.01% Basic Red 76
0.01% Basic Red 51
0.01% HC Red BN
0.01% HC Red 3
0.01% 3-Nitro-p-Hydroxyethylaminophenol
0.05% HC Blue 2
0.05% Basic Blue 26
0.05% Basic Blue 75
3.5% Cetearyl alcohol
1.0% Ceteareth 30
0.5% Glycol Distearate
3.0% Stearamide DEA
1.0% Sodium Oleoamphohydroxypropyl Sulfonate
0.5% Polyquarternium-6
0.1% Tinovis CD (Dimethylacrylamide/Ethyltrimonium Chloride Methacrylate Copolymer, Propylene Glycol Dicaprylate/Dicaprate, PPG-1 Trideceth-6, C10-11 Iso-paraffin) water ad 100% is applied for 30 minutes, at room temperature to bleached human hair, and rinsed. The result is a reddish brown dyeing with good fastnesses.

Example 31

60 ml of part A, 60 ml of part B and 3 ml of part C are mixed in a mixing bowl or applicator bottle and the mixture is immediately applied to a tress of brown hair. After 30 minutes the tress is rinsed, shampooed, rinsed and dried. The tress has been dyed an intensive violet.

| | Shade: Pure Red INGREDIENT | w/w % |
|---|---|---|
| Part A | Deionized Water RT | 20.00 |
| | Sodium Sulfite | 0.60 |
| | Disodium EDTA | 0.05 |
| | Cocamidopropyl Betaine 30% | 4.00 |
| | Propylene Glycol | 2.50 |
| | Monoethanolamine 99% | 1.00 |
| | Toluene-2,5-Diamine Sulfate | 0.25 |
| | p-Aminophenol | 0.50 |
| | 4-Amino-2-Hydroxytoluene | 0.70 |
| | 2-Methyl-5-Hydroxyethylaminophenol | 0.50 |
| | 2-Amino-4-Hydroxyethyl AA Sulfate | 0.10 |
| | Erythorbic Acid | 0.40 |
| | Deionized Water RT | 43.55 |
| | Hydroxyethylcellulose - Natrosol 250 HHR CG | 0.75 |
| | Deionized Water RT | 10.00 |
| | Isopropyl Alcohol | 8.00 |
| | Oleth-10 | 1.00 |
| | Oleic Acid | 1.10 |
| | Lactamide MEA | 1.00 |
| | Fragrance Drom 837 375 Tropical Fever | 0.50 |
| | Dihydroxypropyl PEG-5 Linoleammonium Chloride | 0.50 |
| | Hydrolyzed Soy Protein | 0.50 |
| | Monoethanolamine 99% | ~2.50 |
| | Total: | 100.00 |
| Part B: Developer 6% | Deionized Water RT | 80.50 |
| | Disodium Phosphate | 0.15 |
| | Salcare SC80 | 5.00 |
| | Glycerin 99% | 1.00 |
| | Sodium Laureth Sulfate 27% | 1.00 |
| | Etidronic Acid 60% | ~0.35 |
| | Hydrogen Peroxide 50% | 12.00 |
| | Total: | 100.00 |
| Part C | Deionized Water RT | 99.00 |
| | Basic Blue 26 | 0.3 |
| | Basic Blue 75 | 0.2 |
| | Basic Blue 124 | 0.4 |
| | Basic Red 51 | 0.1 |

Example 32

A dye emulsion, containing 0.4% of Basic Blue 124, 0.3% Basic Blue 76 and 0.3% Basic Blue 75 pH=10.5

| INGREDIENT | w/w % |
|---|---|
| Cetearyl Alcohol | 12.00 |
| Ceteareth-20 | 4.50 |
| Polysorbate 60 | 2.3 |
| Glyceryl Stearate SE | 2.00 |
| Sorbitan Stearate | 0.75 |
| Oleth-5 | 1.25 |
| Caprylic/Capric Triglyceride | 0.50 |
| Deionized Water 70° C. | 66.65 |
| Disodium EDTA | 0.05 |

-continued

| INGREDIENT | w/w % |
|---|---|
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Total: | 100.00 | is mixed with 1.5 weight of 9% hydrogen peroxide solution and the mixture is immediately applied to a tress of brown hair. After 30 minutes the tress is rinsed, shampooed, rinsed and dried. The tress has been dyed an intensive blue.

The invention claimed is:

1. Hair dyeing composition comprising (a) a dye of formula

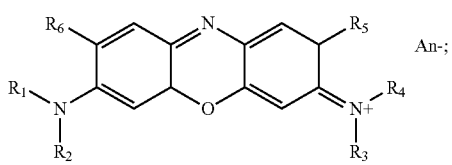

(1)

(b) at least one dye selected from the compounds of formulae

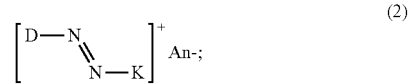

(2)

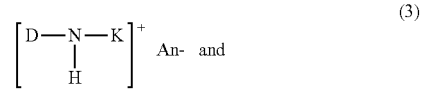

(3)

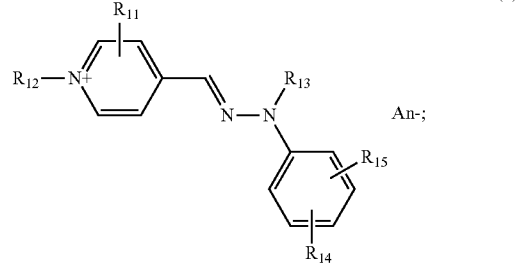

(4)

wherein

D is the radical of a diazo component of the formula

(2a)

-continued

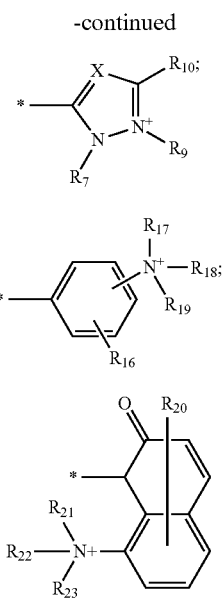

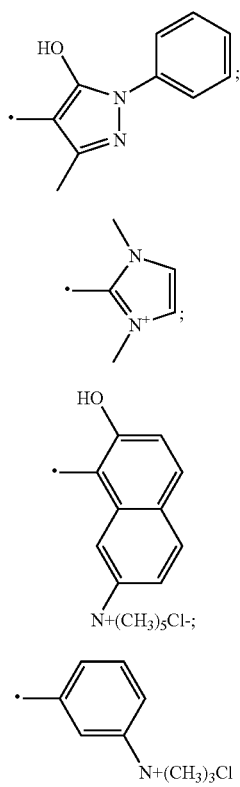

K is the radical of a coupling component selected from aniline derivatives; phenol derivatives; naphthalene derivative;

X is —CH═ —O—; —S—; or —N($R_7$)—;

$R_1$, $R_2$, $R_3$ and $R_4$ independently from each other are hydrogen; or $C_1$-$C_4$alkyl;

$R_5$ and $R_6$ independently from each other are hydrogen; $C_1$-$C_4$alkyl; or $C_1$-$C_4$alkoxy;

$R_7$ and $R_9$ independently from each other are unsubstituted or OH—, $C_1$-$C_4$alkoxy-, halogen-, amino-, $C_1$-$C_4$-mono or -dialkylamino-substituted $C_1$-$C_4$alkyl; or phenyl;

$R_8$ is hydrogen; $C_1$-$C_4$alkyl; Cl; or nitro;

$R_{10}$ is hydrogen; $C_1$-$C_4$alkyl; Cl; nitro; amino; or $C_1$-$C_4$mono- or $C_1$-$C_4$dialkylamino;

$R_{11}$ is hydrogen; $C_1$-$C_4$alkyl; or CN;

$R_{12}$ is unsubstituted or OH—or CN-substituted $C_1$-$C_4$alkyl;

$R_{13}$ is hydrogen; or $C_1$-$C_4$alkyl;

$R_{14}$ and $R_{15}$ independently from each other are hydrogen; $C_1$-$C_4$alkyl; or $C_1$-$C_4$alkoxy; or $R_{14}$ and $R_{15}$ together with the nitrogen and carbon atoms joining them together form a 5-or 6-membered ring;

$R_{16}$ and $R_{20}$ independently from each other are hydrogen; $C_1$-$C_4$alkyl; hydroxy; Cl; nitro; amino, $C_1$-$C_4$mono- or dialkylamino;

$R_{17}$, $R_{18}$, $R_{19}$, $R_{21}$, $R_{22}$ and $R_{23}$ independently from each other are hydrogen; or $C_1$-$C_4$alkyl;

$R_{24}$ is hydrogen; or $C_1$-$C_4$alkyl; and

An⁻ is a colorless anion.

2. Composition according to claim 1, wherein in formula (1) of component (a) $R_1$, $R_2$, $R_3$ and $R_4$ independently from each other are hydrogen; or $C_1$-$C_2$alkyl.

3. Composition according to claim 1, wherein component (a) corresponds to formula

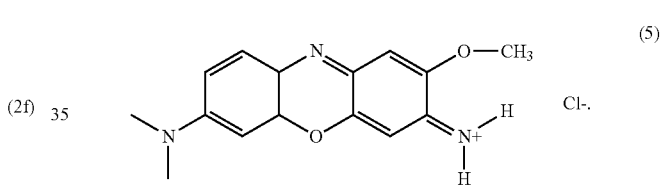

4. Composition according to claim 1, wherein $R_8$ is hydrogen; or $C_1$-$C_4$alkyl.

5. Composition according to claim 1, wherein in formulas (2a) and (2b)

$R_7$ and $R_9$ independently from each other are $C_1$-$C_4$alkyl; or phenyl.

6. Composition according to claim 1, wherein in formula (2a)

X is —N$R_7$; and $R_8$ is hydrogen; or $C_1$-$C_4$alkyl.

7. Composition according to claim 1, wherein in formula (2)

K is the radical of formula

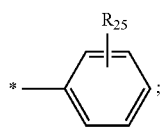

wherein $R_{25}$ is hydrogen; hydroxy; $C_1$-$C_4$alkyl; $C_1$-$C_4$alkoxy; nitro; amino; mono-$C_1$-$C_4$alkylamino; di-$C_1$-$C_4$alkylamino; or a radical of formula

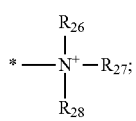

wherein $R_{26}$, $R_{27}$ and $R_{28}$ independently from each other are hydrogen; or $C_1$-$C_4$alkyl.

8. Composition according to claim 1, wherein in formula (3)

K is the radical of formula

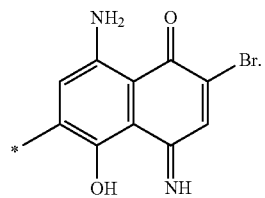

(2k)

9. Composition according to claim 1 comprising (a) a dye of formula (1), and
(b) at least one dye selected from the compounds of formulae

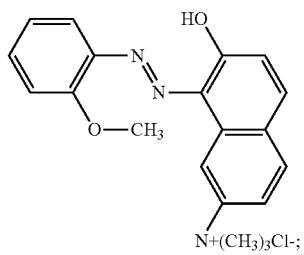

(6)

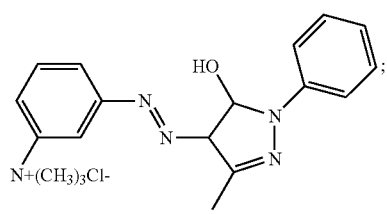

(7)

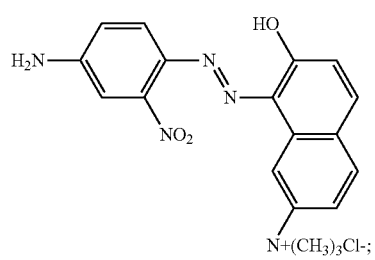

(8)

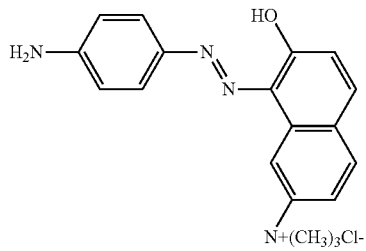

(9)

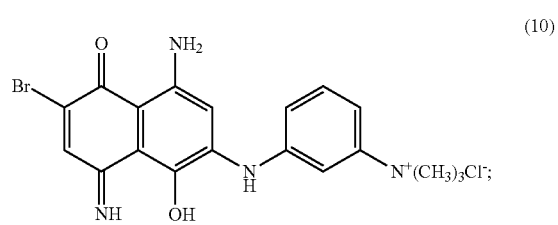

(10)

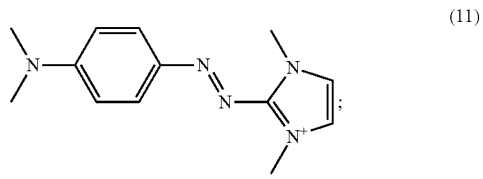

(11)

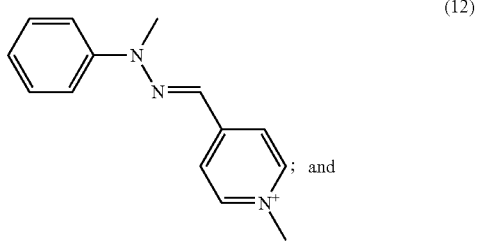

(12) ; and

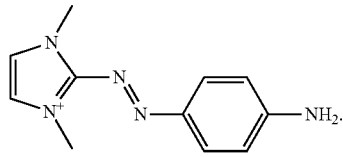

(13)

10. Composition according to claim 1 comprising (a) a dye of formula (1), and
(b) at least one dye selected from the compounds of formulae

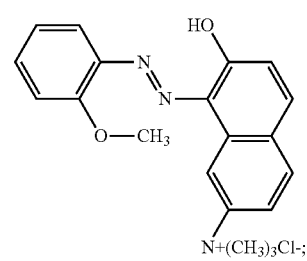

(6)

(7)
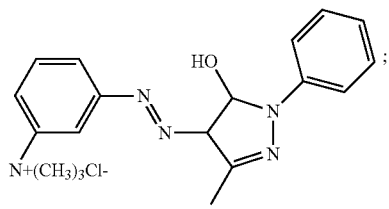

(8)
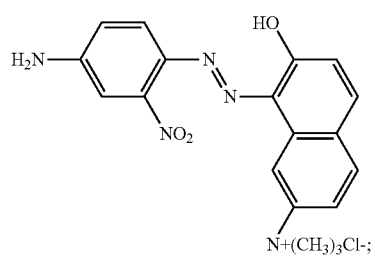

(9)
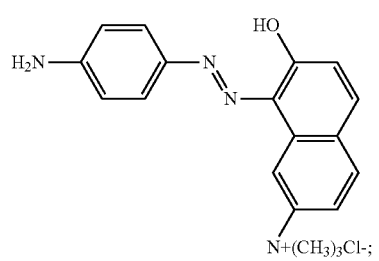

(10)
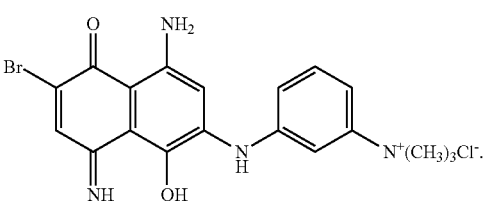

11. Composition according to claim 1 comprising
(a) a dye of formula (1), and
($b_1$) the dyes of formulae (6)
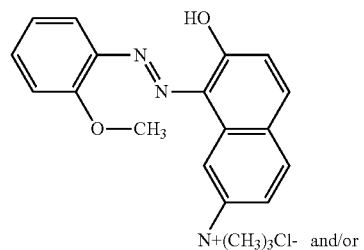

(11)
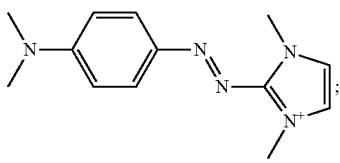

and ($b_2$) the dye of formula

(12)
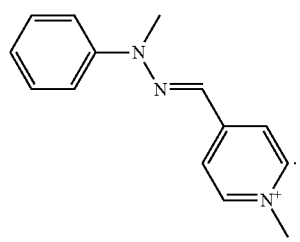

12. Composition according to claim 1 comprising as additional component a colorant selected from (d) a direct dye;

(e) an oxidative dye;

(f) a disulfide dye;

(g) a pigment;

or mixtures thereof.

13. A method for dyeing keratinous fibers, comprising applying the dyeing composition according to claim 1 to said keratinous fibers.

14. A method for dyeing keratinous fibers, comprising the steps of (a) treating the hair with a lightening composition, (b) optionally treating the hair with a reductive wave agent; and (c) treating the hair with a hair dyeing composition according to claim 1.

* * * * *